US010052028B2

(12) United States Patent
Hirota

(10) Patent No.: US 10,052,028 B2
(45) Date of Patent: *Aug. 21, 2018

(54) PHOTOACOUSTIC IMAGING METHOD AND PHOTOACOUSTIC IMAGING APPARATUS

(71) Applicant: FUJIFILM Corporation, Minato-Ku, Tokyo (JP)

(72) Inventor: Kazuhiro Hirota, Kanagawa-ken (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 423 days.

This patent is subject to a terminal disclaimer.

(21) Appl. No.: 15/019,354

(22) Filed: Feb. 9, 2016

(65) Prior Publication Data

US 2016/0150974 A1 Jun. 2, 2016

Related U.S. Application Data

(63) Continuation of application No. 14/036,418, filed on Sep. 25, 2013, now Pat. No. 9,320,475, which is a (Continued)

(30) Foreign Application Priority Data

Mar. 29, 2011 (JP) ................................ 2011-071382
Mar. 8, 2012 (JP) ................................ 2012-051189

(51) Int. Cl.
*A61B 5/05* (2006.01)
*A61B 5/00* (2006.01)

(52) U.S. Cl.
CPC .......... *A61B 5/0095* (2013.01); *A61B 5/0037* (2013.01); *A61B 5/489* (2013.01); *A61B 5/7425* (2013.01); *F04C 2270/041* (2013.01)

(58) Field of Classification Search
None
See application file for complete search history.

(56) References Cited

U.S. PATENT DOCUMENTS

2004/0220465 A1 11/2004 Cafarella
2005/0004458 A1 1/2005 Kanayama et al.
(Continued)

FOREIGN PATENT DOCUMENTS

CN 1650794 A 8/2005
CN 101385638 A 3/2009
(Continued)

OTHER PUBLICATIONS

Communication dated Jul. 16, 2014, issued by the European Patent Office in corresponding Application No. 12763582.9.
(Continued)

*Primary Examiner* — Jonathan Cwern
(74) *Attorney, Agent, or Firm* — Sughrue Mion, PLLC

(57) ABSTRACT

A photoacoustic imaging method that enables photoacoustic images to be displayed at high speed is provided. The photoacoustic imaging method scans a subject with a light beam, detects acoustic waves generated within the subject due to the scanning of light to obtain acoustic wave detected signals, and generates volume data that represent three dimensional photoacoustic images of the subject based on the acoustic wave detected signals. Photoacoustic projection images projected in the direction of irradiation depth of the light are generated, prior to the volume data being generated and concurrently with the scanning of the light. The photoacoustic projection images are displayed.

9 Claims, 11 Drawing Sheets

Related U.S. Application Data continuation of application No. PCT/JP2012/001885, filed on Mar. 19, 2012.

(56) References Cited

U.S. PATENT DOCUMENTS

| | | |
|---|---|---|
| 2005/0187471 A1 | 8/2005 | Kanayama et al. |
| 2006/0239538 A1 | 10/2006 | Sato et al. |
| 2009/0069685 A1 | 3/2009 | Nishihara et al. |
| 2010/0063400 A1 | 3/2010 | Hall et al. |
| 2010/0094134 A1 | 4/2010 | Zhu et al. |
| 2010/0331662 A1 | 12/2010 | Fukutani et al. |
| 2011/0066023 A1 | 3/2011 | Kabushiki et al. |
| 2011/0144496 A1 | 6/2011 | Li et al. |
| 2011/0208057 A1 | 8/2011 | Oikawa |
| 2012/0281902 A1 | 11/2012 | Oikawa et al. |
| 2014/0007690 A1 | 1/2014 | Hirota |

FOREIGN PATENT DOCUMENTS

| | | |
|---|---|---|
| EP | 2684524 A1 | 1/2014 |
| JP | 10-085210 A | 4/1998 |
| JP | 2005-218684 A | 8/2005 |
| JP | 2009-066110 A | 4/2009 |
| JP | 2009-207677 A | 9/2009 |
| JP | 2011-005042 A | 1/2011 |
| JP | 2011-172611 A | 9/2011 |
| WO | 2012/114695 A1 | 8/2012 |

OTHER PUBLICATIONS

Communication dated Jul. 23, 2015 from the European Patent Office in counterpart application No. 12763582.9.

Communication dated Nov. 27, 2014 from the State Intellectual Property Office of P.R. China in counterpart application No. 201280016350.6.

International Search Report of PCT/JP2012/001885 dated May 29, 2012.

Xueding Wang et al., "A High-Speed Photoacoustic Tomography System based on a Commercial Ultrasound and a Custom Transducer Array", Proc. of SPIE, 2010, pp. 75624-1-75624-9, vol. 7564.

PHOTOACOUSTIC IMAGING METHOD AND PHOTOACOUSTIC IMAGING APPARATUS

CROSS REFERENCE TO RELATED APPLICATIONS

This application is a continuation application of Ser. No. 14/036,418 filed Sep. 25, 2013, which is a bypass continuation of the PCT Application No.: PCT/JP2012/001885 filed on Mar. 19, 2012, which claims foreign priority from the Japanese Patent Application No. 2011-071382, filed in the Japanese Patent Office on Mar. 29, 2011 and the Japanese Patent Application No. 2012-051189, filed in the Japanese Patent Office on Mar. 8, 2012, the disclosures of which are incorporated herein by reference in their entirety.

TECHNICAL FIELD

The present invention is related to a photoacoustic imaging method, that is, a method that irradiates light onto a subject such as living tissue, and images the subject based on acoustic waves which are generated accompanying the irradiation of light.

The present invention is also related to an apparatus that executes the photoacoustic imaging method.

BACKGROUND ART

Conventionally, photoacoustic imaging apparatuses that image the interiors of living organisms utilizing the photoacoustic effect are known, as disclosed in U.S. Patent Application Publication No. 20050004458 and X. Wang et al., "A High-Speed Photoacoustic Tomography System based on a Commercial Ultrasound and a Custom Transducer Array", Proc. of SPIE, Vol. 7564, pp. 75624-1-75624-9, 2010. Photoacoustic imaging apparatuses irradiate pulsed light such as pulsed laser beam into the living organisms. Biological tissue that absorbs the energy of the pulsed light generates acoustic waves by volume expansion thereof due to heat. The acoustic waves are detected by an ultrasound probe or the like, and visualizations of the interiors of the living organisms is enabled based on the electrical signals (photoacoustic signals) obtained thereby.

Photoacoustic imaging methods construct images based only on acoustic waves that radiate from specific light absorbers. Therefore, photoacoustic imaging is favorably suited to image specific tissue within living organisms, such as blood vessels. Application of photoacoustic imaging to image and display blood vessels during surgery humans to enable confirmation of the positions of the blood vessels is being considered. In the case that photoacoustic imaging is applied to such a use, so called volume data that represent two dimensional regions of subjects are generated based on photoacoustic signals that represent two dimensional regions of the subjects, and tomographic images of desired cross sections are constructed based on the volume data, as disclosed in U.S. Patent Application Publication No. 20100031662.

DISCLOSURE OF THE INVENTION

In the case that photoacoustic imaging is applied to confirm the positions of blood vessels as described above, it is not necessary to change a slice position a large number of times to observe a large number of tomographic images as in a case for medical diagnosis. It is desired to display photoacoustic images expediently accompanying movement of a probe. However, in the conventional photoacoustic imaging method, volume data are generated, and then photoacoustic images are generated and displayed based on the volume data. Therefore, it had been difficult to display photoacoustic images within short periods of time.

The present invention has been developed in view of the foregoing circumstances. It is an object of the present invention to provide a photoacoustic imaging method capable of displaying photoacoustic images at high speed.

Another object of the present invention is to provide a photoacoustic imaging apparatus capable of executing such a photoacoustic imaging method.

A photoacoustic imaging method of the present invention comprises:

scanning a subject with light;

detecting acoustic waves generated within the subject by the scanning of light to obtain acoustic wave detection signals; and generating volume data that represent three dimensional acoustic images of the subject based on the acoustic wave detection signals;

photoacoustic projection images of the subject projected in the irradiation depth direction of the light being generated based on the acoustic detected signals prior to the volume data being generated and concurrently with the scanning of the light; and the photoacoustic projection images being displayed by a display means.

Note that the expression "concurrently with the scanning of the light" means that the timing at which the photoacoustic projection images are generated and the timing that the light is scanned overlap at least partially. By adopting this configuration, the photoacoustic projection images can be generated and displayed in a so called "real time" manner accompanying the scanning of the light.

Note that in the photoacoustic imaging method of the present invention, it is desirable for:

the absolute values of the acoustic wave detection signals to be integrated with respect to the irradiation depth direction of the light; and for the photoacoustic projection images to be generated based on the values of the integrated acoustic wave detection signals.

In this case, it is desirable for a range in the direction of irradiation depth within which the integration is performed to be able to be set as desired.

In addition, in the photoacoustic imaging method of the present invention, it is desirable for:

photoacoustic tomographic images of planes that extend in the irradiation depth direction of the light to be generated based on the acoustic wave detection signals prior to the volume data being generated and concurrently with the scanning of the light; and for the photoacoustic tomographic images to be displayed by the display means along with the photoacoustic projection images.

In addition, in the photoacoustic imaging method of the present invention, it is desirable for:

the subject to be scanned with acoustic waves concurrently with the scanning with light;

reflected acoustic wave detection signals to be obtained by detecting reflected acoustic waves which are reflected by the subject accompanying the scanning with acoustic waves;

reflected acoustic wave projection images which are projected in the irradiation depth direction of the light to be generated based on the reflected acoustic wave detection signals; and the reflected acoustic wave projection images and the photoacoustic projection images to be displayed in an overlapping manner in a state in which common portions of the subject within the images overlap each other.

In addition, in the photoacoustic imaging method of the present invention, it is desirable for:

the subject to be scanned with acoustic waves concurrently with the scanning with light;

reflected acoustic wave detection signals to be obtained by detecting reflected acoustic waves which are reflected by the subject accompanying the scanning with acoustic waves;

reflected acoustic wave tomographic images of planes that extend in the irradiation depth direction of the light to be generated based on the reflected acoustic wave detection signals; and the reflected acoustic wave tomographic images and the photoacoustic tomographic images to be displayed in an overlapping manner in a state in which common portions of the subject within the images overlap each other.

In addition, in the photoacoustic imaging method of the present invention, it is desirable for:

the subject to be scanned with acoustic waves concurrently with the scanning with light;

reflected acoustic wave detection signals to be obtained by detecting reflected acoustic waves which are reflected by the subject accompanying the scanning with acoustic waves;

reflected acoustic wave tomographic images of planes that extend in the irradiation depth direction of the light to be generated based on the reflected acoustic wave detection signals; and the reflected acoustic wave tomographic images and the photoacoustic projected images to be displayed by the display means.

In addition, in the photoacoustic imaging method of the present invention, it is desirable for:

images that represent blood vessels of living organisms to be generated as the photoacoustic tomographic images.

A photoacoustic imaging apparatus of the present invention comprises:

light scanning means for scanning a subject with light;

acoustic wave detecting means for detecting acoustic waves generated within the subject due to the scanning of light and obtaining acoustic detected signals;

means for generating volume data that represent three dimensional photoacoustic images of the subject based on the acoustic detected signals;

image constructing means for generating photoacoustic projection images of the subject projected in the irradiation depth direction of the light based on the acoustic detected signals prior to the volume data being generated and concurrently with the scanning of the light; and display means for displaying the photoacoustic projection images.

It is desirable for the photoacoustic imaging apparatus of the present invention to adopt a configuration, wherein:

the image constructing means is configured to be capable of generating photoacoustic tomographic images of the subject related to planes that extend in the irradiation depth direction of the light based on the acoustic wave detection signals prior to the volume data being generated and concurrently with the scanning of the light; and the photoacoustic imaging apparatus further comprises:

image combining means for combining the photoacoustic tomographic images and the photoacoustic projection images such that the two types of images are displayed separately by the display means.

It is desirable for the photoacoustic imaging apparatus of the present invention to further comprise:

acoustic wave scanning means for scanning the subject with acoustic waves;

reflected acoustic wave detecting means for detecting acoustic waves reflected by the subject due to the scanning of the acoustic waves and obtaining reflected acoustic detected signals; and image combining means; and wherein:

the image constructing means is configured to be capable of generating reflected acoustic projection images of the subject projected in the irradiation depth direction of the light based on the reflected acoustic detected signals prior to the volume data being generated and concurrently with the scanning of the acoustic waves; and the image combining means combines the reflected acoustic projection images and the photoacoustic projection images such that the two types of images are displayed by the display means in an overlapping manner in a state in which common portions of the subject within the images overlap each other.

It is desirable for the photoacoustic imaging apparatus of the present invention to further comprise:

acoustic wave scanning means for scanning the subject with acoustic waves;

reflected acoustic wave detecting means for detecting acoustic waves reflected by the subject due to the scanning of the acoustic waves and obtaining reflected acoustic detected signals; and image combining means; and wherein:

the image constructing means is configured to be capable of generating reflected acoustic tomographic images of the subject related to planes that extend in the irradiation depth direction of the light based on the reflected acoustic detected signals prior to the volume data being generated and concurrently with the scanning of the acoustic waves; and the image combining means combines the reflected acoustic tomographic images and the photoacoustic projection images such that the two types of images are displayed separately by the display means.

It is desirable for the photoacoustic imaging apparatus of the present invention to further comprise:

acoustic wave scanning means for scanning the subject with acoustic waves;

reflected acoustic wave detecting means for detecting acoustic waves reflected by the subject due to the scanning of the acoustic waves and obtaining reflected acoustic detected signals; and image combining means; and wherein:

the image constructing means is configured to be capable of generating reflected acoustic tomographic images of the subject related to planes that extend in the irradiation depth direction of the light based on the reflected acoustic detected signals prior to the volume data being generated and concurrently with the scanning of the acoustic waves; and the image combining means combines the reflected acoustic tomographic images and the photoacoustic tomographic images such that the two types of images are displayed by the display means in an overlapping manner in a state in which common portions of the subject within the images overlap each other.

It is desirable for the photoacoustic imaging apparatus of the present invention to adopt a configuration, wherein:

the light scanning means is constituted by a holding portion that holds a plurality of light irradiating sections that output the light toward the subject and a plurality of detecting elements of the acoustic wave detecting means arranged in a common single direction, and a moving means for moving the holding portion in a direction perpendicular to the single direction.

Alternatively, the photoacoustic imaging apparatus of the present invention may adopt a configuration, wherein:

the light scanning means is constituted by a plurality of light irradiating sections which are arranged in a two dimensional matrix.

The photoacoustic imaging method of the present invention generates photoacoustic projection images projected in the irradiation depth direction of the scanned light based on acoustic wave detection signals concurrently with the scanning of the light prior to generating volume data, and displays the photoacoustic projection images on the display means. Therefore, photoacoustic projection images can be generated and displayed more expediently compared to a case in which volume data are generated based on acoustic wave detection signals, and then photoacoustic images are generated based on the volume data.

The photoacoustic imaging method of the present invention may generate photoacoustic tomographic images of planes that extend in the irradiation depth direction of the scanned light concurrently with the scanning of light prior to the volume data being generated, and displays the photoacoustic tomographic images along with the photoacoustic projection images on the display means. In this case, photoacoustic tomographic images may also be generated and displayed expediently in addition to the photoacoustic projection images.

The photoacoustic imaging method of the present invention may display the photoacoustic tomographic images and reflected acoustic wave tomographic images in an overlapped manner, or display the photoacoustic projection images and reflected acoustic wave projection images in an overlapped manner. In this case, the positions of blood vessels and the like can be more accurately discriminated, by referring to the reflected acoustic wave images that represent living tissue.

The photoacoustic imaging method of the present invention may integrate the absolute values of photoacoustic signals in the irradiation depth direction of light, and generate photoacoustic projection images based on the integrated values of the photoacoustic signals. In addition, the range in the irradiation depth direction in which integration is to be performed may be set as desired. In this case, the range in the depth direction for which projection images are generated can be changed as desired. By referring to photoacoustic projection images in such a case, whether a tissue system such as blood vessels which may be present along a depth direction is at a position shallower than a predetermined depth or at a position deeper than the predetermined depth can be accurately understood.

The photoacoustic imaging apparatus of the present invention comprises the image constructing means that generates photoacoustic projection images, which are projected in the irradiation depth direction of scanned light, of a subject based on acoustic wave detection signals concurrently with the scanning of the light and prior to volume data being generated, and the display means that displays the photoacoustic projection images. Therefore, the photoacoustic imaging apparatus of the present invention is capable of executing the photoacoustic imaging method of the present invention.

BEST MODE FOR CARRYING OUT THE INVENTION

Figure 1:
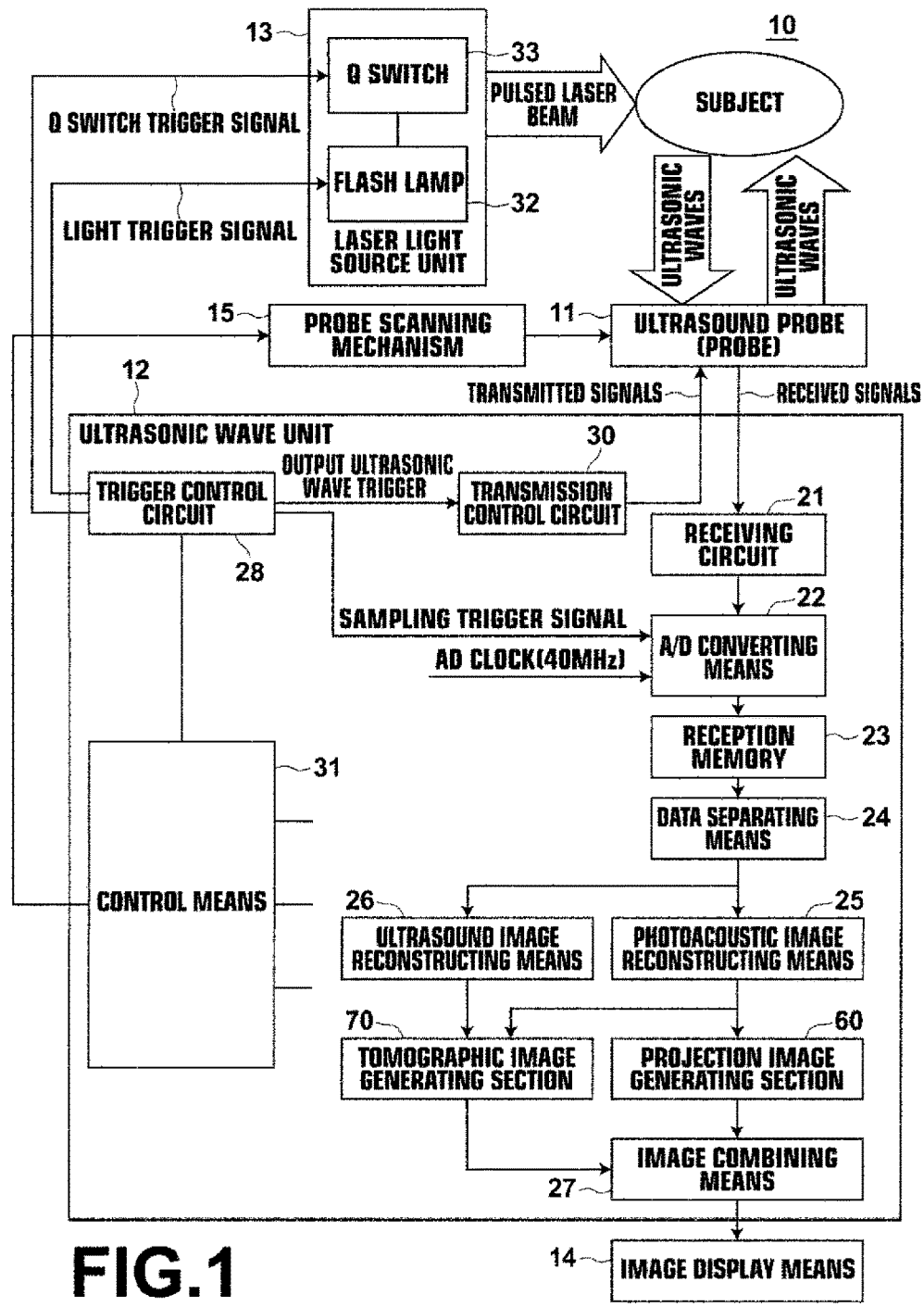
FIG. 1 is a block diagram that illustrates the schematic configuration of a photoacoustic imaging apparatus that executes a photoacoustic imaging method according to a first embodiment of the present invention.

Hereinafter, embodiments of the present invention will be described in detail with reference to the attached drawings. FIG. 1 illustrates a photoacoustic imaging apparatus 10 according to a first embodiment of the present invention. The photoacoustic imaging apparatus 10 includes: an ultrasound probe (probe) 11; an ultrasonic wave unit 12; and a laser light source (laser unit) 13. The laser unit 13 generates a laser beam to be irradiated onto subject. The wavelength of the light beam to be irradiated onto subjects may be set as appropriate according to targets of observation. The laser beam output by the laser unit 13 is guided to the probe 11 by a light guiding means such as an optical fiber, then irradiated onto subjects from the probe 11.

The probe 11 further outputs (transmits) ultrasonic waves to subjects as a type of acoustic wave, and detects (receives) reflected ultrasonic waves reflected by the subjects. The probe 11 has a plurality of ultrasonic transducers which are arranged one dimensionally, for example. The probe 11 also detects ultrasonic waves (acoustic waves) which are generated by targets of measurement within subjects absorbing the laser beam output by the laser unit 13. The end portions of the light guiding means, that is, the leading end portions of a plurality of optical fibers or the like, are arranged along the arrangement direction of the plurality of ultrasonic transducers, and the laser beam is irradiated toward the subjects therefrom.

Figure 4:
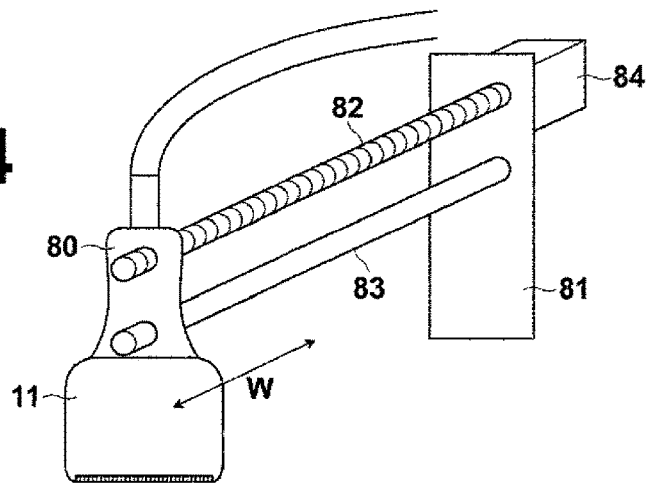
FIG. 4 is a perspective view that illustrates a scanning mechanism employed by the apparatus of FIG. 1.

Note that when photoacoustic images or ultrasonic images of subjects are obtained, the probe 11 is moved in a direction substantially perpendicular to the direction in which the ultrasonic transducers and the end portions of the light guiding means extend, to thereby two dimensionally scan the subjects with the laser beam and the ultrasonic waves. This scanning may be performed by an operator manually moving the probe 11. Alternatively, a scanning mechanism such as that illustrated in FIG. 4 may be employed to realize more precise two dimensional scanning. The scanning mechanism illustrated in FIG. 4 is constituted by: a threaded engagement portion 80 which is coupled to the probe 11; a holding plate 81; a bore screw 82 which is rotatably held by the holding plate 81 and is in threaded engagement with the threaded engagement portion 80; a guide rod 83 which is fixed to the holding plate 81 and passes through an aperture of the threaded engagement portion 80; and a motor 84 for rotating the bore screw 82 in the clockwise and counterclockwise directions. When the motor 84 of the scanning mechanism is driven, the threaded engagement portion 80 which is in threaded engagement with the rotating bore screw 82 advances and retreats, the probe 11 moves in the direction of arrow W in FIG. 4, and the two dimensional scanning described above is realized.

Returning to FIG. 1, the ultrasonic wave unit 12 has a receiving circuit 21, an A/D converting means 22, a reception memory 23, a data separating means 24, photoacoustic image reconstructing means 25, a projection image generating section 60 that receives the output of the photoacoustic image reconstructing means 25, an ultrasound image reconstructing means 26, a tomographic image generating section 70 that receives the output of the ultrasound image reconstructing means 26 and the output of photoacoustic image reconstructing means 25; and an image combining means 27 that receives the output of the tomographic image generating section 70 and the output of the projection image generating section 60. The ultrasonic wave unit 12 further includes: a trigger control circuit 28, a transmission control circuit 30, and a control means 31. The control means 31 controls each component of the ultrasonic wave unit 12.

The probe 11 detects the acoustic waves and outputs acoustic wave detection signals. The probe 11 also detects the reflected ultrasonic waves and outputs ultrasonic wave detection signals. The receiving circuit 21 receives the acoustic wave detection signals and the ultrasonic wave detection signals. The A/D converting means 22 is a sampling means, and converts the acoustic wave detection signals and the ultrasonic wave detection signals received by the receiving circuit 21 into digital signals. The A/D converting means 22 samples each type of signal at a predetermined sampling period synchronized with an A/D clock signal, for example.

The trigger control circuit 28 outputs a light trigger signal that commands light output to the laser unit 13. The laser unit 13 includes a flash lamp 32 which si a pumping light source for a Q switch pulse laser such as YAG or titanium sapphire, and a Q switch 33 that controls laser oscillation. When the trigger control circuit 28 outputs a flash lamp trigger signal, the laser unit 13 lights the flash lamp 32 and pumps the Q switch pulse laser. The trigger control circuit 28 outputs a Q switch trigger signal after the flash lamp 32 sufficiently pumps the Q switch pulse laser, for example. The Q switch is turned ON when the Q switch trigger signal is received, and causes a laser beam to be output from the laser unit 13. The amount of time required from the timing that the flash lamp 32 is lit to a point in time at which the Q switch laser is sufficiently pumped can be estimated from the properties of the Q switch laser.

Note that the Q switch 33 may be turned ON within the laser unit 13 instead of the Q switch being controlled by the trigger control circuit 28. In this case, a signal that indicates that a Q switch has been turned ON may be transmitted to the ultrasonic wave unit 12 from the laser unit 13.

In addition, the trigger control circuit 28 outputs an ultrasonic wave trigger signal that commands ultrasonic wave transmission to the transmission control circuit 30. The trigger control circuit 28 outputs the light trigger signal first, and then outputs the ultrasonic wave trigger signal thereafter. That is, the trigger control circuit 28 outputs the ultrasonic wave trigger signal following output of the light trigger signal. Irradiation of a laser beam onto a subject and detection of acoustic waves are performed by the light trigger signal being output, and transmission of ultrasonic waves toward the subject and detection of reflected ultrasonic waves are performed thereafter by output of the ultrasonic wave trigger signal.

The sampling control circuit 29 further outputs a sampling trigger signal that commands initiation of sampling to the A/D converting means 22. The sampling control circuit 29 outputs a sampling trigger signal at a timing following output of a light trigger signal by the trigger control circuit 28 and prior to output of an ultrasonic wave trigger signal. The sampling control circuit 29 outputs a sampling trigger signal at a timing following output of the light trigger signal, and preferably at a timing at which a laser beam is actually irradiated onto a subject. For example, the sampling control circuit 29 outputs a sampling trigger signal synchronized with the timing at which the trigger control circuit 28 outputs a Q switch trigger signal. When the sampling trigger signal is received, the A/D converting means 22 initiates sampling of ultrasonic waves (photoacoustic signals) detected by the probe 11.

Following output of the light trigger signal, the trigger control circuit 28 outputs an ultrasonic wave trigger signal at a timing that detection of acoustic waves is completed. At this time, the A/D converting means 22 does not interrupt sampling of ultrasonic wave signals, but continues to execute sampling. In other words, the trigger control circuit 28 outputs the ultrasonic wave trigger signal in a state in which the A/D converting means 22 is continuing sampling of the ultrasonic wave signals. The target of detection of the probe 11 changes from acoustic waves to reflected ultrasonic waves, by the probe 11 transmitting ultrasonic waves in response to the ultrasonic wave trigger signal. The A/D converting means 22 continuously samples the photoacoustic waves and the reflected acoustic waves, by continuing sampling of detected ultrasonic wave signals.

The A/D converting means 22 stores both the sampled photoacoustic signals and the sampled reflected ultrasonic wave detection signals in the common reception memory 23. The sampled data stored in the reception memory 23 are data of acoustic wave detection signals up to a certain point in time, and become data of reflected ultrasonic wave detection signals after the point in time. The data separating means 24 separates the acoustic wave detection signals and the ultrasonic wave signals stored in the reception memory 23. The data separating means 24 provides the separated acoustic wave detection signals to the photoacoustic image reconstructing means 25, and provides the separated ultrasonic wave signals to the ultrasound image reconstructing means 26.

The photoacoustic image reconstructing means 25 and the ultrasound image reconstructing means 26 are capable of generating volume data that represent three dimensional regions of subjects. However, in the method of the present embodiment, projection images and tomographic images to be described later are generated prior to the volume data being generated. The functions regarding this point will be described hereinafter.

The photoacoustic image reconstructing means 25 adds data from 64 ultrasonic transducers of the probe 11 at delay times corresponding to the positions of the ultrasonic transducers, to generate data corresponding to a single line (delayed addition method), for example. Alternatively, the photoacoustic image reconstructing means 25 may execute image reconstruction by the CBP (Circular Back Projection) method. As further alternatives, the photoacoustic image reconstructing means 25 may execute image reconstruction by the Hough transform method or Fourier transform method. The ultrasound image reconstructing means 26 also generates data corresponding to each line of ultrasound images, which are tomographic images, from data generated based on the ultrasonic wave detection signals.

Figure 2:
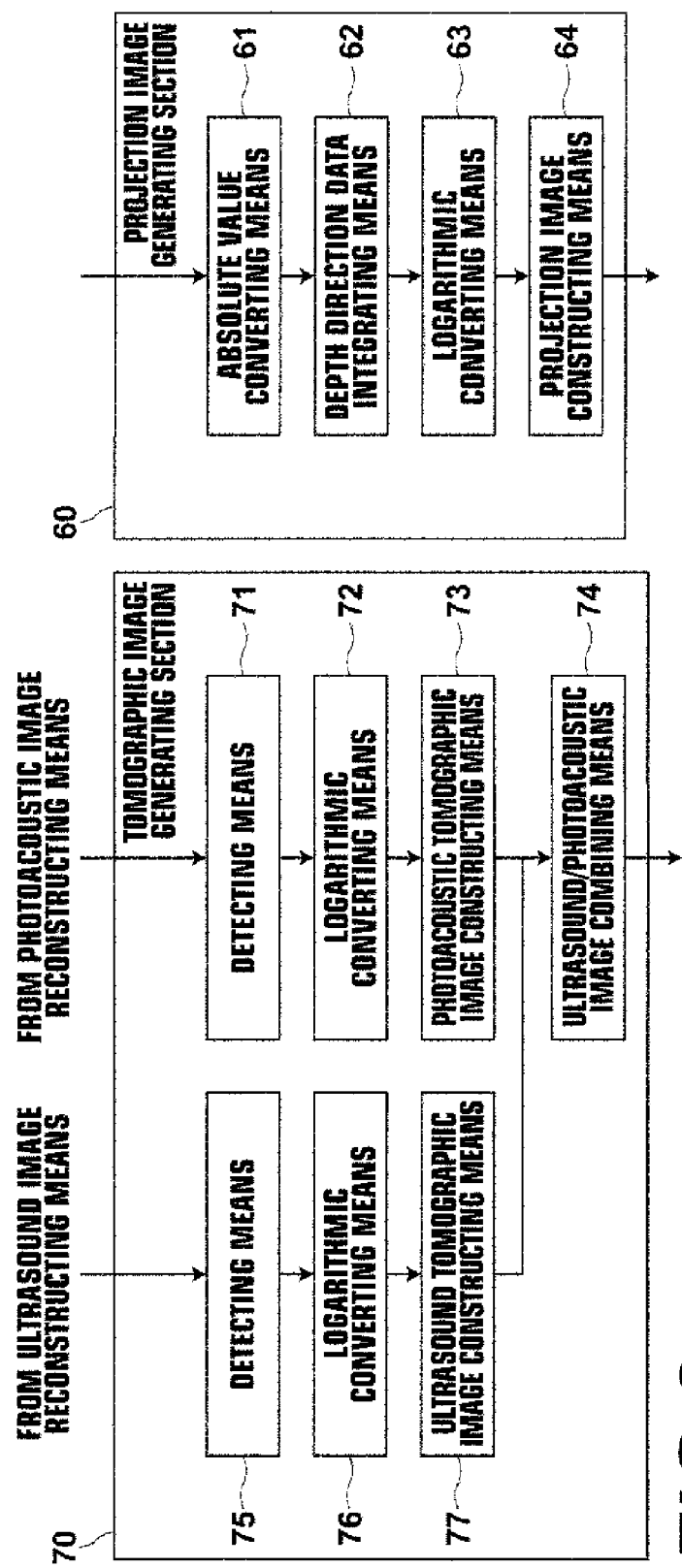
FIG. 2 is a block diagram that illustrates a portion of the configuration illustrated in FIG. 1.

FIG. 2 illustrates the detailed configuration of the projection image generating section 60, into which reconstructed image data generated by the photoacoustic image reconstructing means 25 are input, and the tomographic image generating section 70, into which reconstructed image data generated by the photoacoustic image reconstructing means 25 and reconstructed image data generated by the ultrasound image reconstructing means 25 are input.

As illustrated in FIG. 2, the projection image generating section 60 includes: a absolute value converting means 61, into which reconstructed image data generated by the photoacoustic image reconstructing means 25 are input; a depth direction data integrating means 62; a logarithmic converting means 63; and a projection image constructing means 64, which are connected in this order. The projection image generating section 60 generates photoacoustic projection images projected in the irradiation depth direction of the laser mean. Note that generation of the photoacoustic projection images will be described in detail later.

Also as illustrated in FIG. 2, the tomographic image generating section 70 includes: a detecting means 71, into which reconstructed image data generated by the photoacoustic image reconstructing means 25 are input; a logarithmic converting means 72; and a photoacoustic tomographic image constructing means 73, which are connected in this order. The tomographic image generating section 70 further includes: a detecting means 75, into which reconstructed image data generated by the ultrasound image reconstructing means 26 are input; a logarithmic converting means 76; and a ultrasound tomographic image constructing means 77, which are connected in this order. The photoacoustic tomographic image constructing means 73 and the ultrasound tomographic image constructing means 77 are connected to an ultrasound/photoacoustic image combining means 74.

The detecting means 71 generates envelope curves of data that represent each line output by the photoacoustic image reconstructing means 25. The logarithmic converting means 72 logarithmically converts the envelope curves to widen the dynamic ranges thereof. The photoacoustic tomographic image constructing means 73 generates photoacoustic tomographic images based on data that represent each line, on which logarithmic conversion has been administered. In greater detail, the photoacoustic tomographic image constructing means 73 generates photoacoustic tomographic images by converting the positions of acoustic wave detection signals (peak portions) along a temporal axis to positions in the depth direction of the photoacoustic tomographic images, for example.

The detecting means 75, the logarithmic converting means 76, and the ultrasound tomographic image constructing means 77 function in the same basic manner as the detecting means 71, the logarithmic converting means 72, and the photoacoustic tomographic image constructing means 73, and generate ultrasound tomographic images. The ultrasound tomographic images, the photoacoustic tomographic images, and the photoacoustic projection images are generated concurrently with the scanning of the laser beam.

The ultrasound/photoacoustic image combining means 74 receive data that represent the photoacoustic tomographic images and data that represent the ultrasound tomographic images generated in the manner described above. The ultrasound/photoacoustic image combining means 74 combines the two types of images such that they will be displayed in an overlapped state, in which common portions of the subject within the images overlap each other. A combined tomographic image which is generated in this manner and a photoacoustic projection image generated by the projection image generating section 60 are combined by the image combining means 27 of FIG. 1 such that they are displayed at different positions, and the images are ultimately displayed by the image display means 14.

Figure 3:
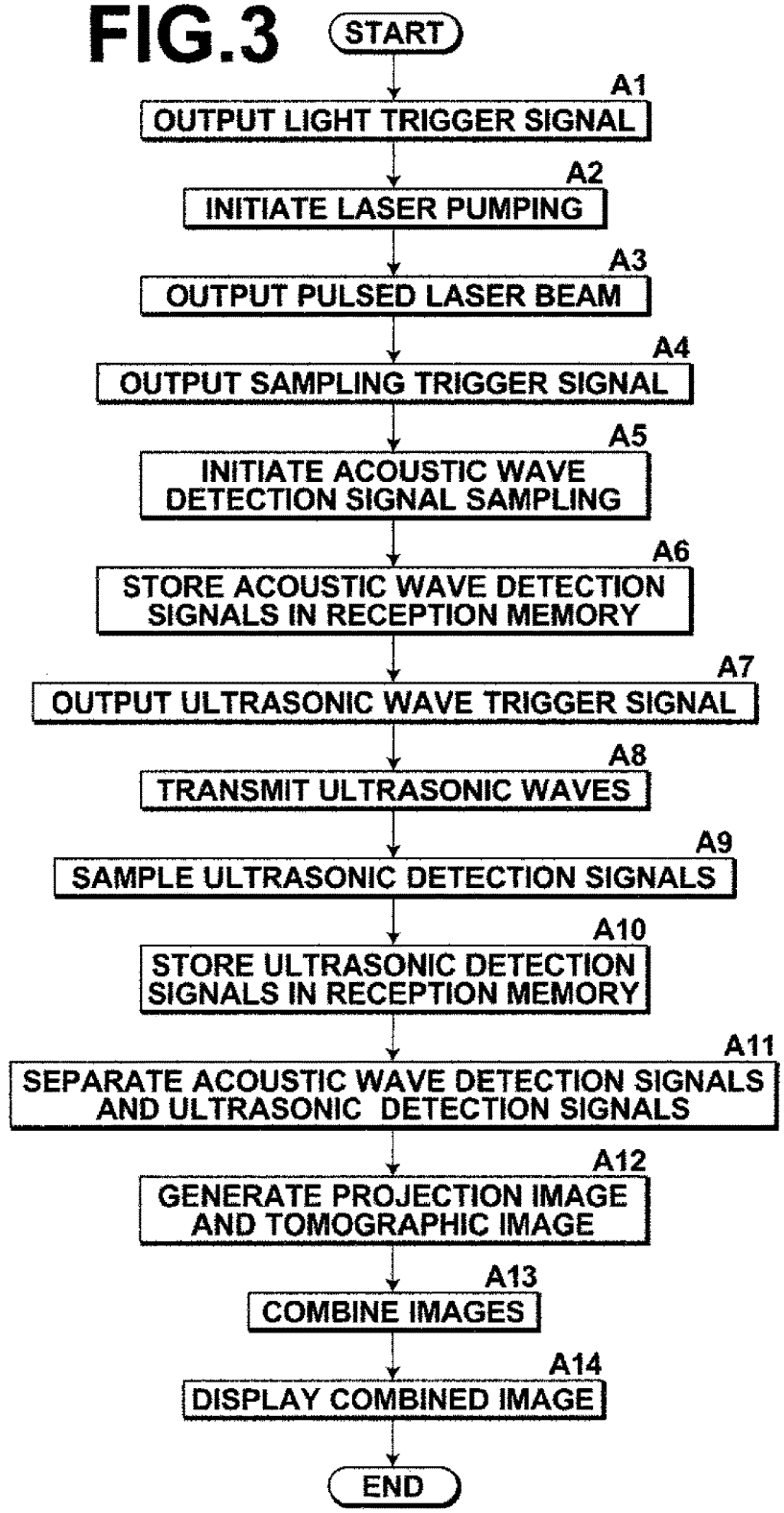
FIG. 3 is a flow chart that illustrates the flow of processes in the photoacoustic imaging method.

FIG. 3 is a flow chart that summarizes the flow of processes described above. First, a light trigger signal is output (A1), pumping of the laser is initiated (A2), and a pulsed laser beam is output (A3). Next, a sampling trigger signal is output (A4), sampling of acoustic wave detection signals is initiated (A5), and the acoustic wave detection signals are stored in the reception memory (A6). Then, an ultrasonic wave trigger signal is output (A7), ultrasonic waves are transmitted (A8), reflected ultrasonic waves are received and ultrasonic wave detection signals are sampled (A9), and the ultrasonic wave detection signals are stored in the reception memory (A10). Next, the acoustic wave detection signals and the ultrasonic wave detection signals are separated (A11), a photoacoustic projection image and a tomographic image (an image in which a photoacoustic tomographic image and an ultrasound tomographic image are overlapped) are generated (A12), the photoacoustic projection image and the tomographic image are combined such that they are displayed separately (A13), and the images are displayed by the image display means (A14).

Figure 5:
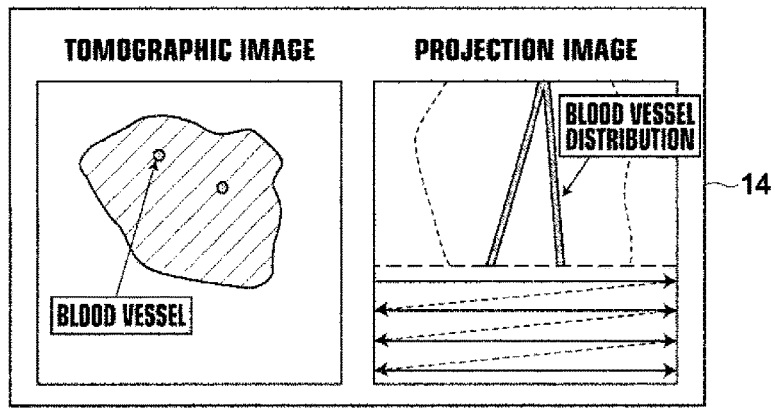
FIG. 5 is a schematic diagram that illustrates an example of images displayed by the photoacoustic imaging method.

FIG. 5 is a schematic diagram that illustrates an example of images which are displayed by the image display means 14 by the processes described above. As illustrated in the right side of FIG. 5, a photoacoustic projection image represents a blood vessel distribution, for example. Here, the scanning of the laser beam is indicated by a horizontal arrow. As the scanning processes, projection images of the scanned range are successively displayed. A photoacoustic tomographic image related to a single cross section represented by the broken horizontal line is displayed at the left side of FIG. 5 as an image that represents the position of a blood vessel when viewed in the cross sectional direction. In the present embodiment, the photoacoustic tomographic image and the ultrasound tomographic image that represents tissue systems of the subject (the portion indicated by hatching in FIG. 5) are displayed in a positionally aligned and overlapped manner. Therefore, the positions of blood vessels within tissue systems can be clearly discriminated.

Figure 6:
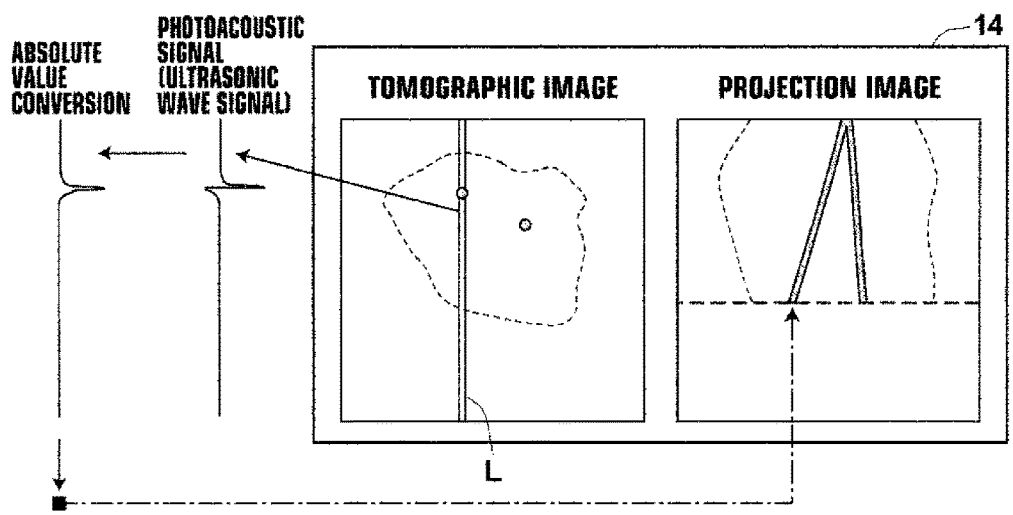
FIG. 6 is a diagram for explaining generation of a photoacoustic projection image.

Here, generation of the photoacoustic projection images will be described with reference to FIG. 2 and FIG. 6. As illustrated in the left side of FIG. 6, if a single line L that extends in the laser beam irradiation depth direction within a tomographic image is considered, photoacoustic signals related to portions (blood vessels, for example) that expand and contract in volume due to light absorption will change from positive to negative (this applies to ultrasonic wave signals as well). Therefore, the absolute value converting means 61 of FIG. 2 obtains the absolute values of these signals, and the absolute values of the signals are integrated by the depth direction data integrating means 62. The integrated value will correspond to an integrated value of light absorption of a portion along the line L. Accordingly, integrated values are obtained for the entire region which is scanned by light, and imaged by the projection image constructing means 64 illustrated in FIG. 2. Thereby, projection images that represent portions at which light absorption occurs can be obtained. Note that the logarithmic converting means 63 illustrated in FIG. 2 is basically the same as the logarithmic converting means 72.

As described above, the present embodiment generates photoacoustic projection images projected in the irradiation depth direction of the scanned light as well as photoacoustic tomographic images related to a plane that extends in the irradiation depth direction of the scanned light based on acoustic wave detection signals concurrently with the scanning of the light prior to generating volume data, and displays the images on the display means 14. Therefore, photoacoustic projection images and photoacoustic tomographic images can be generated and displayed more expediently compared to a case in which volume data are generated based on acoustic wave detection signals, and then photoacoustic images are generated based on the volume data.

Figure 7:
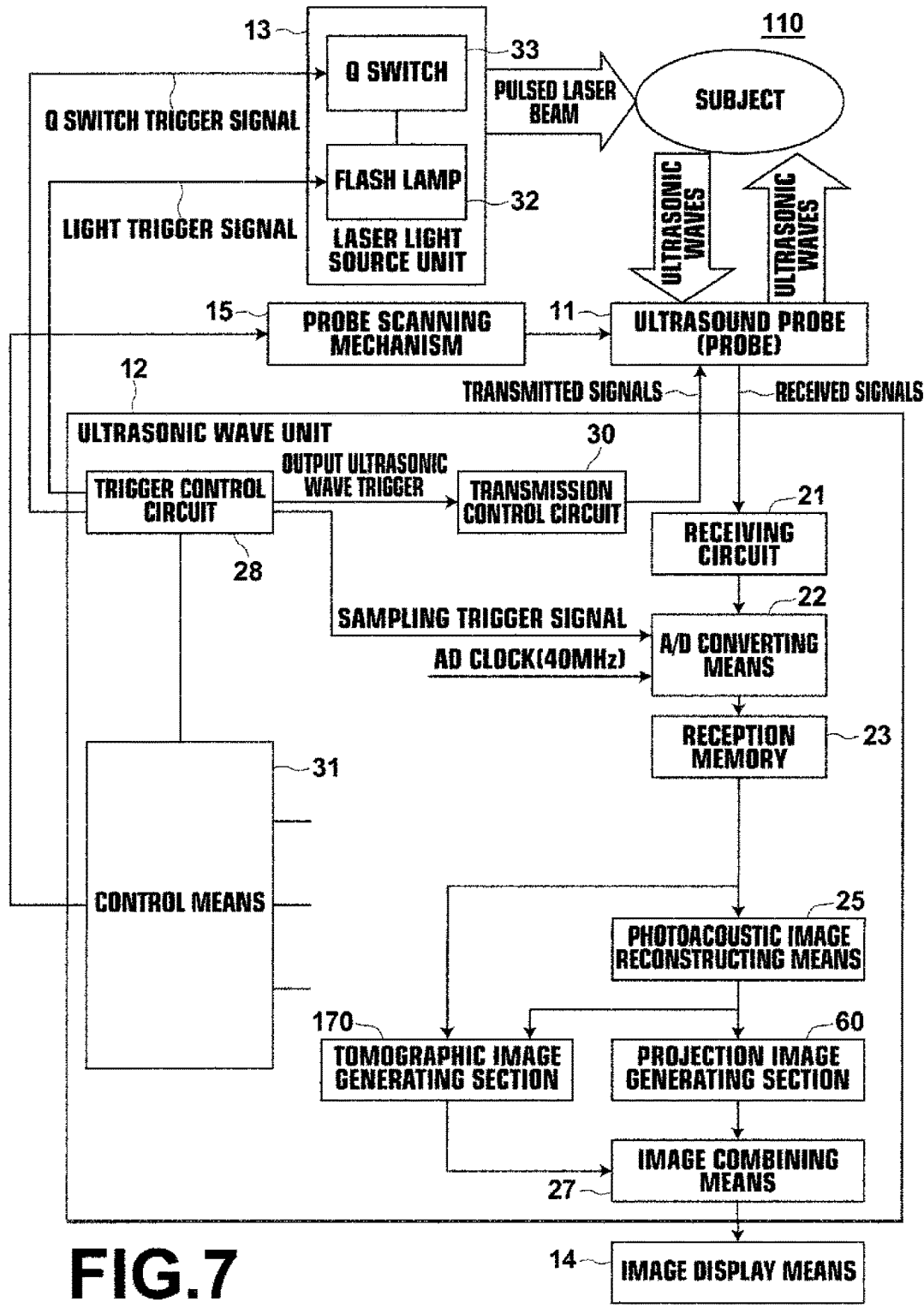
FIG. 7 is a block diagram that illustrates the schematic configuration of a photoacoustic imaging apparatus that executes a photoacoustic imaging method according to a second embodiment of the present invention.
Figure 8:
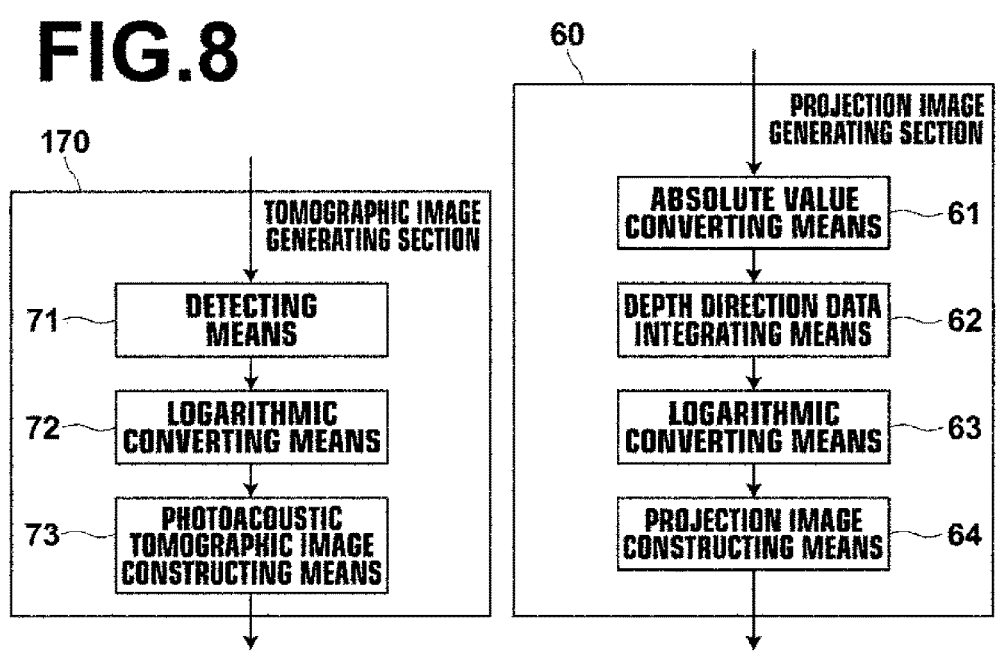
FIG. 8 is a block diagram that illustrates a portion of the configuration illustrated in FIG. 7.

Next, a photoacoustic imaging method according to a second embodiment of the present invention will be described. FIGS. 7 and 8 illustrate a photoacoustic imaging apparatus 110 that executes the method of the second embodiment. FIG. 7 illustrates the basic configuration of the photoacoustic imaging apparatus 110, and FIG. 8 illustrates a projection image generating section 60 and a tomographic image generating section 170 of the photoacoustic imaging apparatus 110 in detail. Note that in FIGS. 7 and 8, constituent elements which are the same as those illustrated in FIGS. 1 and 2 are denoted by the same reference numerals, and detailed descriptions thereof will be omitted insofar as they are not particularly necessary (this applies to all following embodiments).

The method of the present embodiment does not generate ultrasound images. Comparing the photoacoustic imaging apparatus 110 with the photoacoustic imaging apparatus 10 of FIG. 1, the data separating means 24 and the ultrasound image reconstructing means 26 are omitted, and the tomographic image generating section 170 which is illustrated in detail in FIG. 8 is employed instead of the tomographic image generating section 70. Note that the projection image generating section 60 is the same as that employed in the photoacoustic imaging apparatus 10 of FIG. 1.

The tomographic image generating section 170 is basically constituted by the detecting means 71, the logarithmic converting means 72, and the photoacoustic tomographic image constructing means 73 illustrated in FIG. 2, and only generates photoacoustic tomographic images. That is, ultrasound tomographic images are not generated, and therefore photoacoustic tomographic images are not displayed in an overlapped manner with ultrasound tomographic images. Photoacoustic tomographic images generated by the tomographic image generating section 170 are displayed along with photoacoustic projection images generated by the projection image generating section 60 by the image display means 14.

In the present embodiment as well, photoacoustic projection images projected in the irradiation depth direction of the scanned light as well as photoacoustic tomographic images related to a plane that extends in the irradiation depth direction of the scanned light are generated based on acoustic wave detection signals concurrently with the scanning of the light prior to generating volume data, and the photoacoustic images are displayed on the display means 14. Therefore, photoacoustic projection images and photoacoustic tomographic images can be generated and displayed more expediently compared to a case in which volume data are generated based on acoustic wave detection signals, and then photoacoustic images are generated based on the volume data.

The photoacoustic imaging method of the present invention is not limited to the display formats for projection images and tomographic images described above, and the images may be displayed in other formats. Table 1 below illustrates examples of alternate display formats. Note that in Table 1, "Photoacoustic+Ultrasound" refers to overlapped display of the two types of images.

TABLE 1

| Display Format | Tomographic Images | Projection Images |
|---|---|---|
| 1 | Photoacoustic | Photoacoustic |
| 2 | Ultrasound | Photoacoustic |
| 3 | Photoacoustic + Ultrasound | Photoacoustic |
| 4 | Photoacoustic + Ultrasound | Photoacoustic + Ultrasound |

The first embodiment which was described previously employs Display Format 3 of Table 1, and the second embodiment employs Display Format 1.

Figure 9:
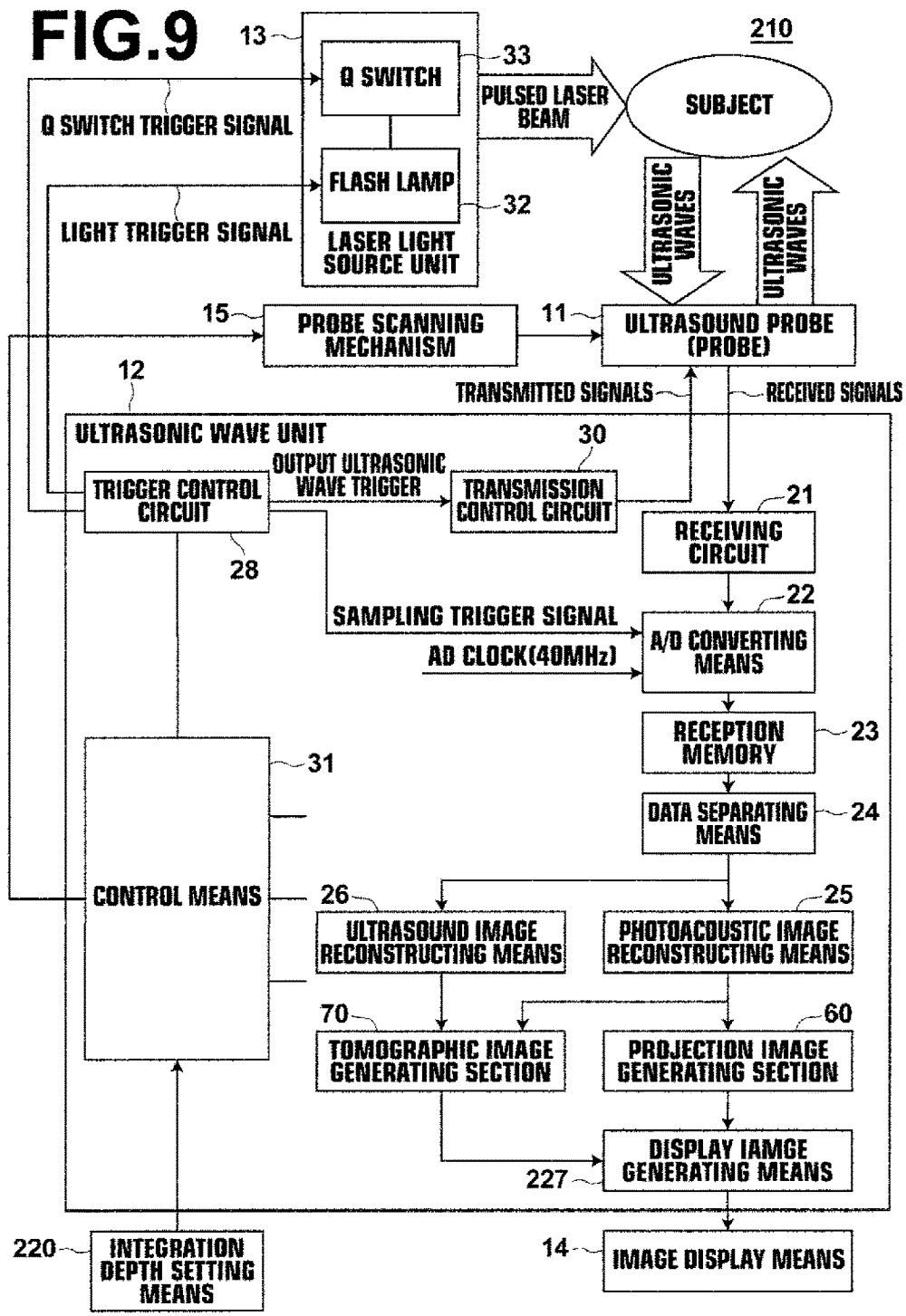
FIG. 9 is a block diagram that illustrates the schematic configuration of a photoacoustic imaging apparatus that executes a photoacoustic imaging method according to a third embodiment of the present invention.

Next, a photoacoustic imaging method according to a third embodiment of the present invention will be described. FIG. 9 illustrates the basic configuration of a photoacoustic imaging apparatus 210 that executes the method of the third embodiment. Comparing the photoacoustic imaging apparatus 210 with the photoacoustic imaging apparatus 10 of FIG. 1, a display image generating means 227 is provided instead of the image combining means 27, and an integrating depth setting means 220 is further provided.

The integrating depth setting means 220 sets the depth from the surface of a subject, for example, to which the depth direction data integrating means 62 of the projection image generating section 60 (refer to FIG. 2) performs integrating processes. For example, the integrating depth setting means 220 is constituted by a keyboard for inputting depths as numerical values, a mouse that moves a cursor displayed by the image display means 14 that indicates a depth position, or the like. Data regarding the integrating depth set by the integrating depth setting means 220 are input to the control means 31. The control means 31 controls the integrating process performed by the depth direction data integrating means 62 such that data are integrated to a position at a depth indicated by the input data.

The display image generating means 227 causes photoacoustic projection images generated by the projection image generating section 60 for the set integrating depth and ultrasound tomographic images generated by the tomographic image generating section 70 by the image display means 14 in so called "real time" concurrently with scanning by the probe 11, for example. Note that as described previously, "concurrently" means that the timing at which the photoacoustic projection images are displayed and the timing that the light is scanned overlap at least partially.

Figure 12:
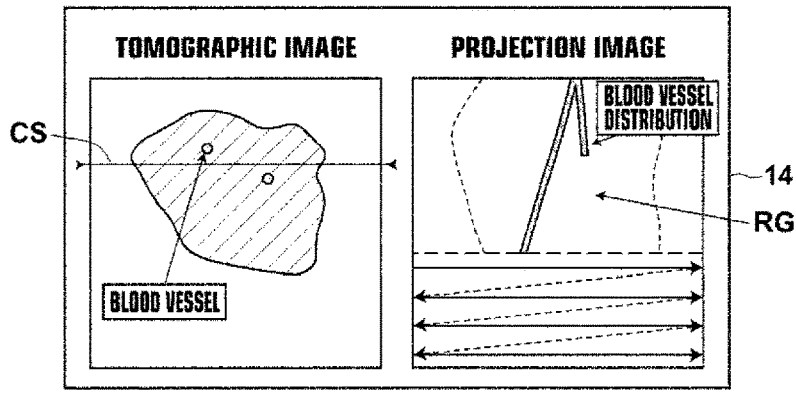
FIG. 12 is a schematic diagram that illustrates an example of images displayed by the apparatus of FIG. 9.

FIG. 12 illustrates an example of an ultrasound tomographic image and a photoacoustic projection image which are displayed in the manner described above. Note that in this example, the aforementioned cursor CS is displayed within the ultrasound tomographic image illustrated at the left side of FIG. 12.

In this example, if the integrating depth is not set, that is, if the integrating depth is not limited, a blood vessel distribution that extends from the upper side of the drawing sheet will be displayed in region RG of the photoacoustic projection image at the right side of FIG. 12. In contrast, by setting the integrating depth, blood vessels which are present at positions deeper than the set depth will not be displayed, as illustrated in FIG. 12. Accordingly, if the depth is set to the maximum depth that could be cut by a scalpel during surgery, all blood vessels displayed in the photoacoustic projection image can be recognized as those that may possibly be cut by a scalpel. In such a case, blood vessels being cut by scalpels can be positively prevented by avoiding the blood vessels displayed in the photoacoustic projection image during surgery.

In contrast, in the case that the integrating depth is not set, all blood vessels, including those present at positions too deep to be cut by a scalpel, are displayed in photoacoustic projection images. Therefore, locations that need not be avoided may also be discriminated as locations that should not be cut by a scalpel. Further, cases in which surgeons mistakenly think that they have cut blood vessels although in actuality, the blood vessels are not cut because they are at deep positions are also entirely possible. Therefore, a problem arises, that regions to be avoided when cutting with scalpels become ambiguous. This problem can be prevented from occurring by setting the integrating depth as described above.

Figure 10:
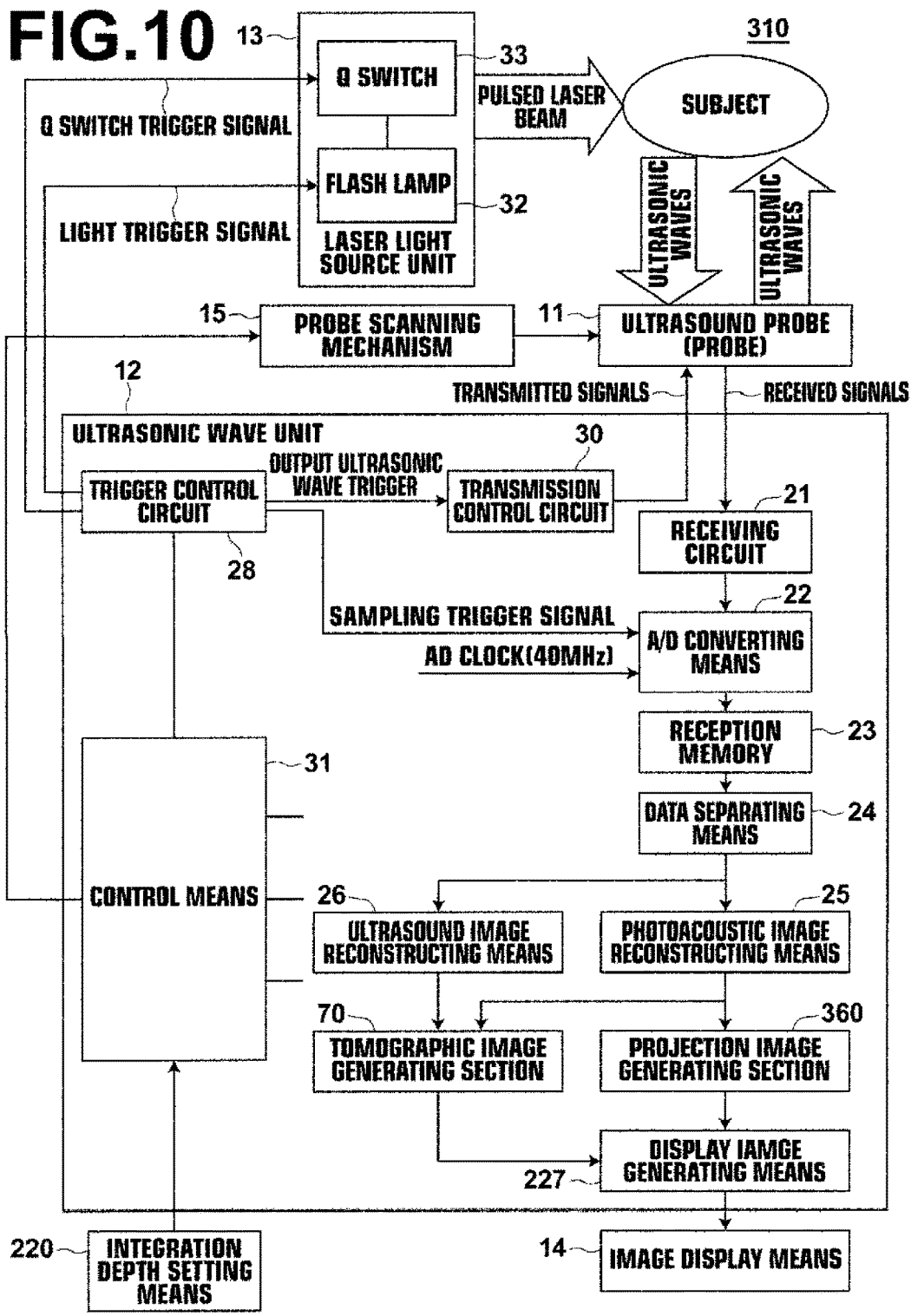
FIG. 10 is a block diagram that illustrates the schematic configuration of a photoacoustic imaging apparatus that executes a photoacoustic imaging method according to a fourth embodiment of the present invention.

Next, a photoacoustic imaging method according to a fourth embodiment of the present invention will be described. FIG. 10 illustrates the basic configuration of a photoacoustic imaging apparatus 310 that executes the method of the fourth embodiment. Comparing the photoacoustic imaging apparatus 310 with the photoacoustic imaging apparatus 210 of FIG. 9, the photoacoustic imaging apparatus 310 is different in that a projection image generating section 360, the detailed configuration of which is illustrated in FIG. 11, is provided instead of the projection image generating section 60.

Figure 11:
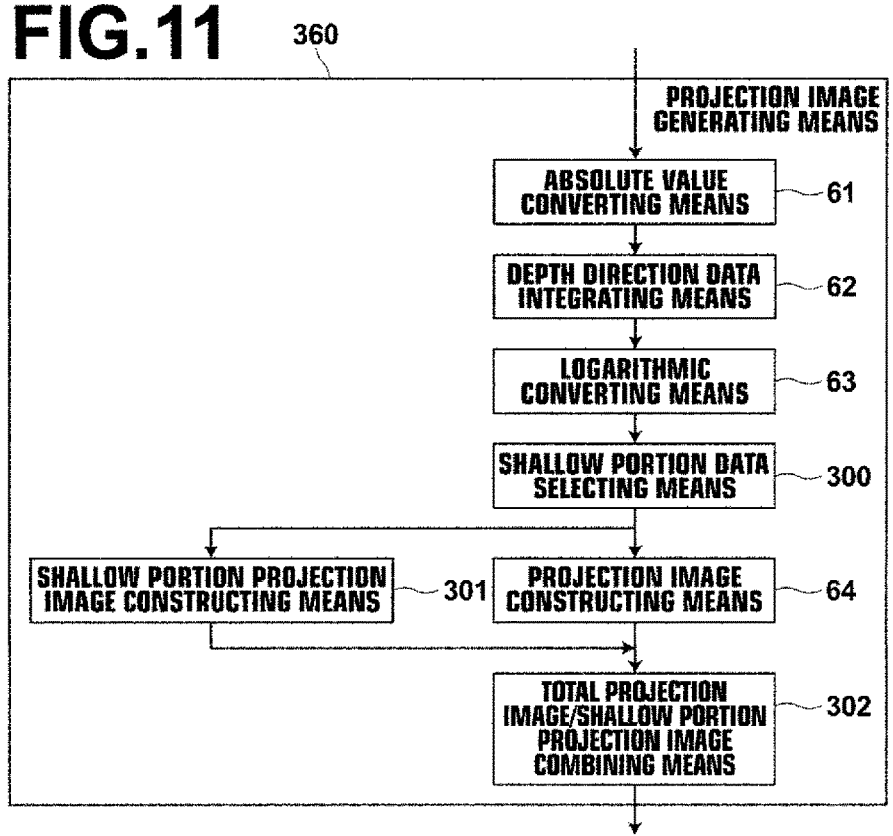
FIG. 11 is a block diagram that illustrates a portion of the configuration illustrated in FIG. 10.

The projection image generating section 360 illustrated in FIG. 11 differs from the projection image generating section 60 of FIG. 2 in that the projection image generating section 360 further includes: a shallow portion data selecting means 300 provided prior to the projection image constructing means 64, a shallow portion projection image constructing means 301 that receives input from the shallow portion data selecting means 300, and a whole projection image/shallow portion projection image combining means 302 that receives input from the projection image constructing means 64 and the shallow portion projection image constructing means 301.

The depth direction data integrating means 62 of the projection image generating section 360 performs integrating processes without setting an integrating depth, that is, without limiting the integrating depth. Accordingly, the projection image constructing means constructs photoacoustic projection images (whole projection images) in which the integrating depth is not limited, in the same manner as the photoacoustic imaging apparatus 10 of the first embodiment illustrated in FIG. 1.

Data output from the logarithmic converting means 63 is also input to the shallow portion data selecting means 300. The shallow portion data selecting means 300 selects and extracts data up to a predetermined depth. The selected and extracted data are output to the shallow portion projection image constructing means 301. Note that the depth to which data are selected is set by the integrating depth setting means 220 of FIG. 10. The shallow portion projection image constructing means 301 employs only data related to the selected shallow portions to construct photoacoustic projection images (shallow portion projection images). The shallow portion projection images which are constructed in this manner are similar to projection images which are constructed after the depth direction data integrating means 62 performing integrating processes with a limited integrating depth.

Figure 13:
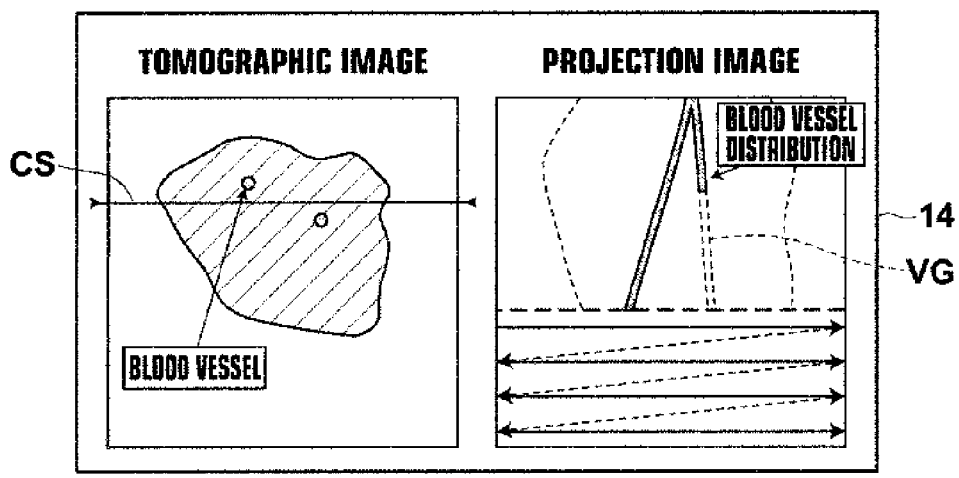
FIG. 13 is a schematic diagram that illustrates an example of images displayed by the apparatus of FIG. 10.

The whole projection images constructed by the projection images constructing means 64 and the shallow portion projection images constructed by the shallow portion projection image constructing means 301 are combined by the whole projection image/shallow portion projection image combining means 302, and the combined projection images are displayed by the image display means 14 of FIG. 10. FIG. 13 illustrates an example of a combined and displayed photoacoustic projection image along with an ultrasound tomographic image. Here, a projection image (shallow portion projection image) similar to that in the example illustrated in FIG. 12 is displayed, and a whole projection image VG is displayed in a region RG, at which nothing is displayed in the example of FIG. 12. The whole projection image VG is displayed at a lower density or in a display color different from that of the shallow portion projection image so as to be distinguishable. The image displayed by the image display means 14 of the present embodiment enables discrimination of what is present up to a predetermined depth as in the display example of the third embodiment illustrated in FIG. 12, and also enables discrimination of what is present at deeper regions.

Figure 14:
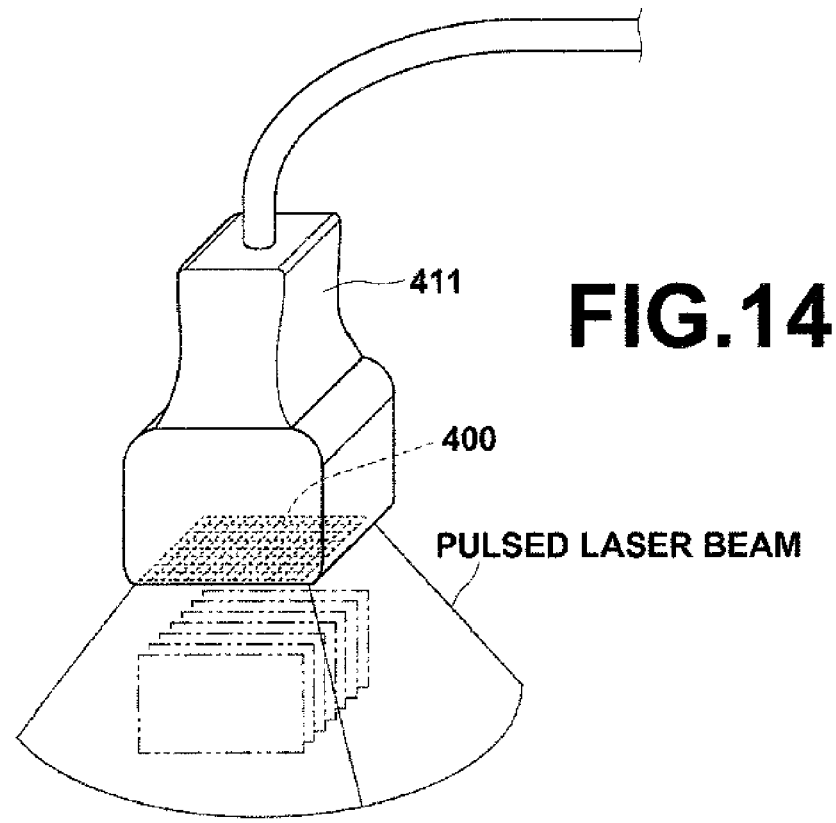
FIG. 14 is a perspective view that illustrates a two dimensional probe employed by a photoacoustic imaging method according to a fifth embodiment of the present invention.
Figure 15:
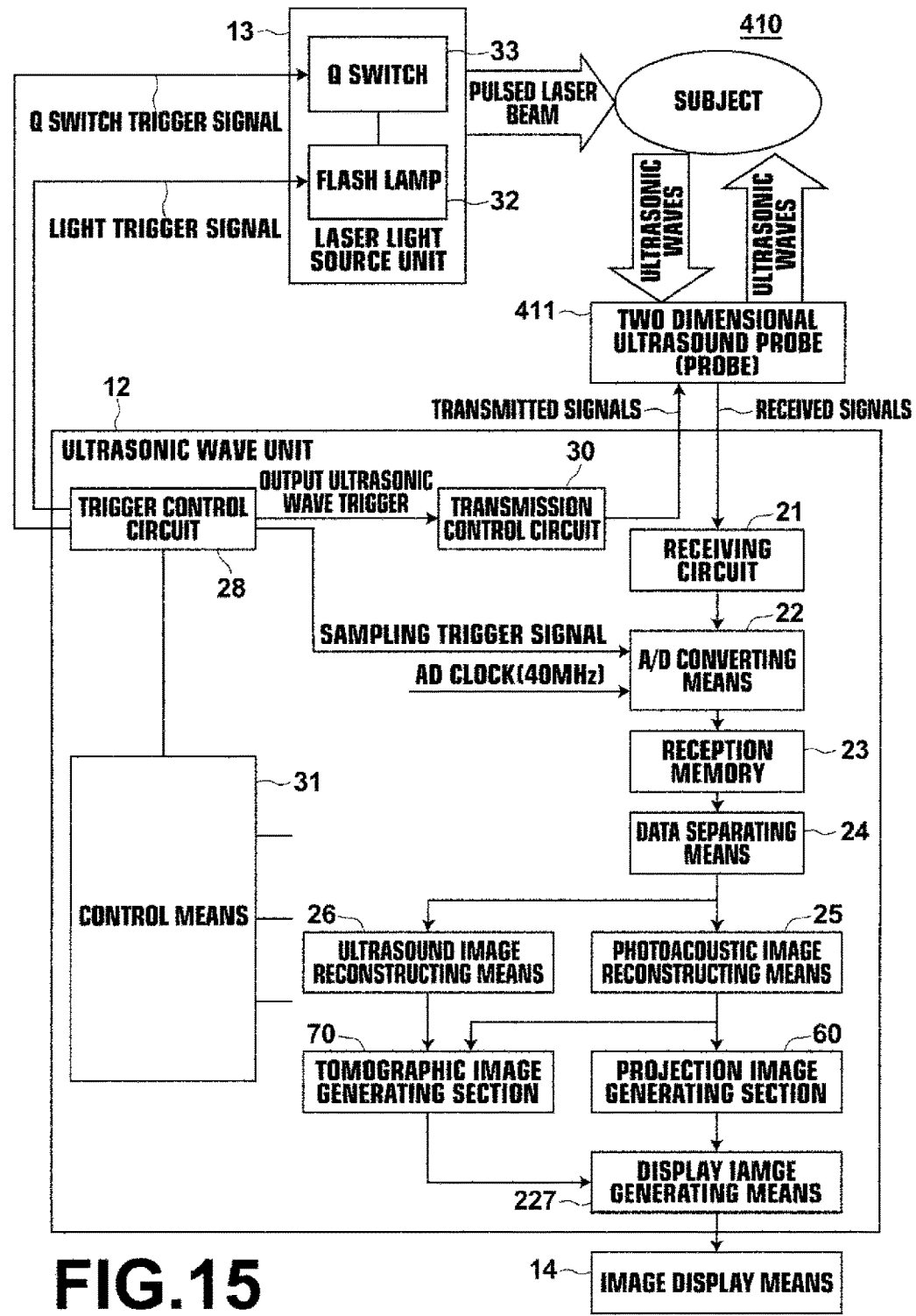
FIG. 15 is a block diagram that illustrates the schematic configuration of a photoacoustic imaging apparatus that executes a photoacoustic imaging method according to the fifth embodiment of the present invention.

Next, a photoacoustic imaging apparatus according to a fifth embodiment of the present invention will be described. FIG. 14 illustrates a two dimensional ultrasound probe (probe) 411 which is employed in the method of the fifth embodiment. FIG. 15 illustrates the basic configuration of a photoacoustic imaging apparatus 410 that executes the method. Comparing the photoacoustic imaging apparatus 410 with the photoacoustic imaging apparatus 210 of FIG. 9, the photoacoustic imaging apparatus 410 is different in that a the two dimensional probe 411 is employed instead of the probe 11, and the probe scanning mechanism 15 is omitted.

As illustrated in FIG. 14, the two dimensional probe 411 is of a structure in which a plurality of light output portions 400 such as the aforementioned light output ends of optical fibers are arranged in a two dimensional matrix. Note that ultrasonic transducers for detecting acoustic waves generated due to light irradiation are omitted from FIG. 14, but are provided paired with each light output end, or provided to surround the plurality of light output portions 400 which are arranged in a two dimensional matrix. The two dimensional probe 411 is capable of irradiating pulsed laser beams corresponding to each cross section onto a subject, as schematically illustrated by the broken line in FIG. 14. The positions onto which light is irradiated can be sequentially changed in a direction perpendicular to an irradiating surface.

That is, the two dimensional probe 411 enables subjects to be scanned with pulsed laser beams without employing a scanning mechanism such as that illustrated in FIG. 4. Photoacoustic projection images are generated by the projection image generating section 60 based on data corresponding to each cross section obtained by scanning the subject in the same manner as in the previously described embodiments. The generated projection images are displayed by the image display means 14 in real time.

Note that light may be irradiated from all of the light output portions 400 which are arranged in a two dimensional simultaneously, and data may be obtained for each cross section instead of irradiating light corresponding to each cross section of a subject.

Preferred embodiments of the present invention have been described above. However, the photoacoustic imaging apparatus and the photoacoustic imaging method are not limited to the above embodiments. Various changes and modifications to the configurations of the above embodiments are included in the scope of the present invention.

What is claimed is:

1. A photoacoustic imaging method, comprising:
    scanning a subject with light;
    detecting acoustic waves generated within the subject by the scanning of light in order to obtain acoustic wave detection signals;
    generating a two-dimensional photoacoustic projection image of the subject line by line, each line of the two-dimensional photoacoustic projection image being projected in an irradiation depth direction of the light, wherein the generating of each line is based on the acoustic detected signals prior to volume data being generated and concurrently with the scanning of the light;
    generating the volume data that represent a three dimensional acoustic image of the subject based on the acoustic wave detection signals; and
    displaying the photoacoustic projection image by a display section line by line.

2. A photoacoustic imaging method as defined in claim 1, further comprising:
    integrating absolute values of the acoustic wave detection signals with respect to the irradiation depth direction of the light; and
    wherein the each line of the photoacoustic projection image is generated based on the integrated values of the absolute values of acoustic wave detection signals.

3. A photoacoustic imaging method as defined in claim 2, further comprising:
    setting a range in the direction of irradiation depth within which the integration is performed as desired.

4. A photoacoustic imaging method as defined in claim 1, further comprising:
    generating photoacoustic tomographic images of planes that extend in the irradiation depth direction of the light based on the acoustic wave detection signals prior to the volume data being generated and concurrently with the scanning of the light; and
    displaying the photoacoustic tomographic images by the display section along with the photoacoustic projection image.

5. A photoacoustic imaging method as defined in claim 4, further comprising:
    scanning the subject with acoustic waves concurrently with the scanning with light in order to obtain reflected acoustic wave detection signals;
    obtaining reflected acoustic wave detection signals by detecting reflected acoustic waves which are reflected by the subject accompanying the scanning with acoustic waves;
    generating reflected acoustic wave tomographic images of planes that extend in the irradiation depth direction of the light based on the reflected acoustic wave detection signals; and
    displaying the reflected acoustic wave tomographic images and the photoacoustic tomographic images in an overlapping manner in a state in which common portions of the subject within the images overlap each other.

6. A photoacoustic imaging method as defined in claim 4, further comprising:
    generating images that represent blood vessels of living organisms as the photoacoustic tomographic images.

7. A photoacoustic imaging method as defined in claim 1, further comprising:
    scanning the subject with acoustic waves concurrently with the scanning with light;
    obtaining reflected acoustic wave detection signals by detecting reflected acoustic waves which are reflected by the subject accompanying the scanning with acoustic waves;
    generating a reflected acoustic wave projection image of the subject line by line, each line of the reflected acoustic wave projection image being projected in the irradiation depth direction of the light based on the reflected acoustic wave detection signals; and
    displaying the reflected acoustic wave projection image and the photoacoustic projection image in an overlapping manner line by line in a state in which common portions of the subject within the images overlap each other.

8. A photoacoustic imaging method as defined in claim 1, further comprising:
    scanning the subject with acoustic waves concurrently with the scanning with light in order to obtain reflected acoustic wave detection signals;
    obtaining reflected acoustic wave detection signals by detecting reflected acoustic waves which are reflected by the subject accompanying the scanning with acoustic waves;
    generating reflected acoustic wave tomographic images of planes that extend in the irradiation depth direction of the light based on the reflected acoustic wave detection signals; and
    displaying the reflected acoustic wave tomographic images and the photoacoustic projected image by the display section.

9. The photoacoustic imaging method of claim 1, wherein:
    the subject is continuously scanned with the light and concurrently the each line of the two dimensional photoacoustic projection image is generated such that while a second cross section of the subject is being scanned, a line of the two dimensional photoacoustic projection image for a first cross section of the subject is generated.

* * * * *